United States Patent
Maehana et al.

(10) Patent No.: US 10,527,616 B2
(45) Date of Patent: *Jan. 7, 2020

(54) **METHOD FOR DETECTING *STAPHYLOCOCCUS* CONTAINED IN MILK**

(71) Applicant: ASAHI KASEI KABUSHIKI KAISHA, Tokyo (JP)

(72) Inventors: Koji Maehana, Tokyo (JP); Kenji Matsuyama, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,384

(22) Filed: Nov. 8, 2018

(65) Prior Publication Data

US 2019/0079089 A1  Mar. 14, 2019

Related U.S. Application Data

(62) Division of application No. 15/105,440, filed as application No. PCT/JP2014/083459 on Dec. 17, 2014, now Pat. No. 10,151,751.

(30) Foreign Application Priority Data

Dec. 18, 2013 (JP) .................. 2013-261823

(51) Int. Cl.
| | | |
|---|---|---|
| *C12N 1/06* | (2006.01) | |
| *G01N 33/569* | (2006.01) | |
| *C12Q 1/14* | (2006.01) | |
| *C12N 9/52* | (2006.01) | |
| *G01N 33/558* | (2006.01) | |

(52) U.S. Cl.
CPC ......... *G01N 33/56938* (2013.01); *C12N 9/52* (2013.01); *C12Q 1/14* (2013.01); *C12Y 304/24075* (2013.01); *G01N 33/558* (2013.01); *G01N 2333/31* (2013.01); *G01N 2333/952* (2013.01); *G01N 2333/96486* (2013.01)

(58) Field of Classification Search
None
See application file for complete search history.

(56) References Cited

U.S. PATENT DOCUMENTS

| | | |
|---|---|---|
| 2010/0099115 A1 | 4/2010 | Mach et al. |
| 2012/0329050 A1 | 12/2012 | Nadeau et al. |

FOREIGN PATENT DOCUMENTS

| | | |
|---|---|---|
| EP | 0359873 B1 | 9/1993 |
| JP | 01-244370 | 9/1989 |
| JP | 02-083336 A | 3/1990 |
| JP | 11-028099 | 2/1999 |
| JP | 2003-171291 | 6/2003 |
| JP | 2006-246792 A | 9/2006 |
| JP | 2007-146030 A | 6/2007 |
| JP | 2010-154851 A | 7/2010 |
| JP | 2012-122921 A | 6/2012 |
| WO | WO 2005/064016 A1 | 7/2005 |

OTHER PUBLICATIONS

Ali-Vehmas et al., "Binding of *Staphylococcus aureus* to Milk Fat Globules Increases Resistance to Penicillin-G", Journal of Dairy Research, vol. 64 (1997) pp. 253-260.
Extended European Search Report for European Application No. 14871368.8, dated Jul. 13, 2017.
International Preliminary Report on Patentability issued in International Application No. PCT/JP2014/083459 dated Jun. 30, 2016.
International Search Report issued in International Application No. PCT/JP2014/083459 dated Mar. 31, 2015.
Schindler et al., "Lysostaphin: A New Bacteriolytic Agent for the *Staphylococcus*," Proceedings of the National Academy of Sciences of the USA, vol. 51, No. 3, 1964 (Communicated Jan. 16, 1964), pp. 414-421.

*Primary Examiner* — Jennifer E Graser
(74) *Attorney, Agent, or Firm* — Birch, Stewart, Kolasch & Birch, LLP

(57) ABSTRACT

The object is to provide a lysis method, lysis treatment solution, detection method using an immunochromatographic device, and detection kit comprising an immunochromatographic device for detecting whether causative bacterium of mastitis is a *staphylococcus* or not by using milk of a livestock animal. There is provided a method for lysing a *staphylococcus*, which comprises the step of mixing a lysis agent containing a lytic enzyme, and at least one kind of ampholytic surfactant, and preferably further containing at least one kind of nonionic surfactant, with milk obtained form a livestock animal to lyse a *staphylococcus* existing in the milk. The lytic enzyme is preferably lysostaphin.

16 Claims, 2 Drawing Sheets

[Fig. 1]
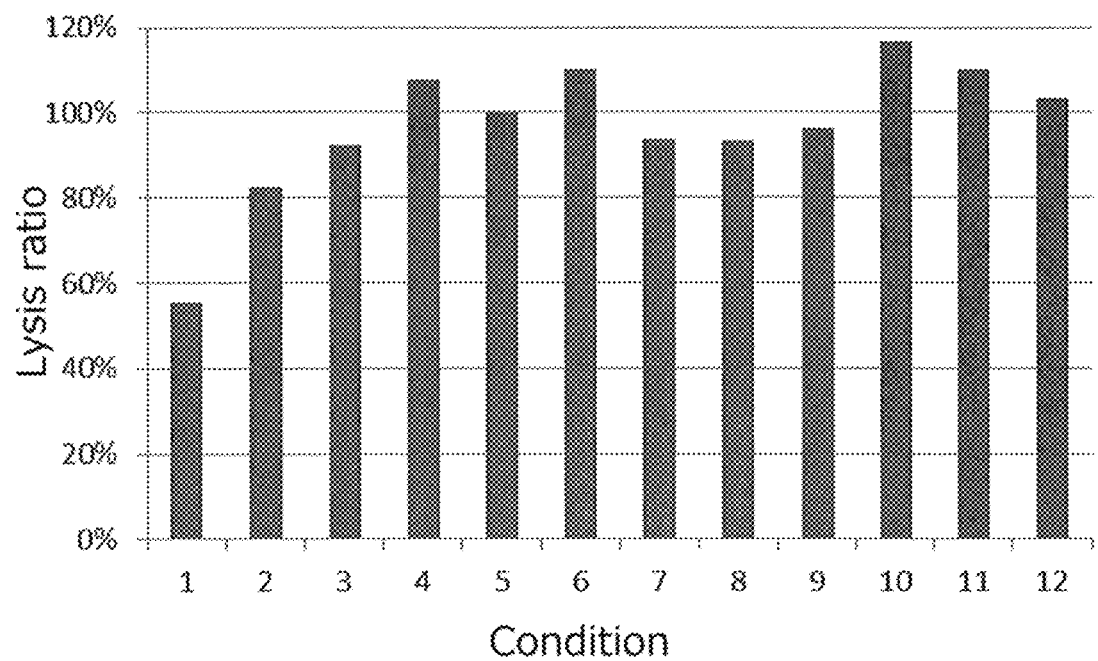
[Fig. 2]
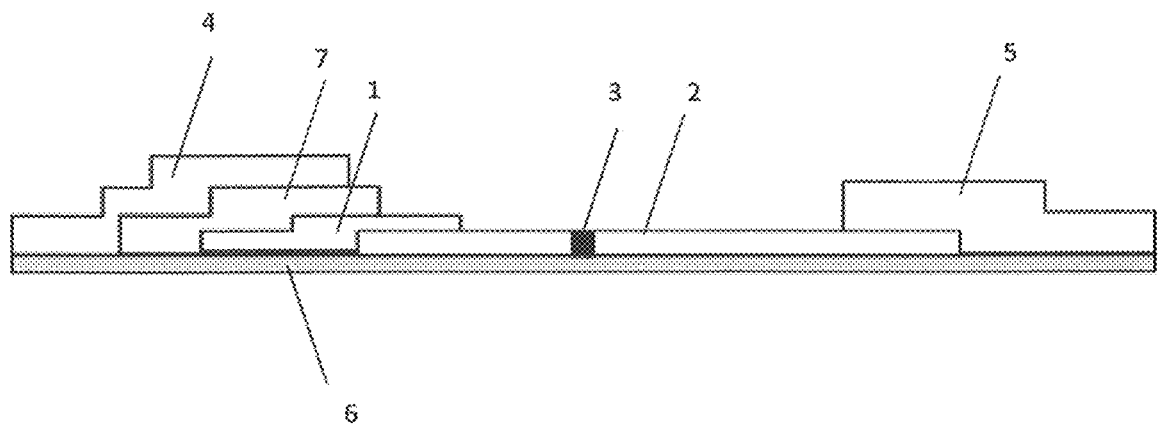

[Fig.3]
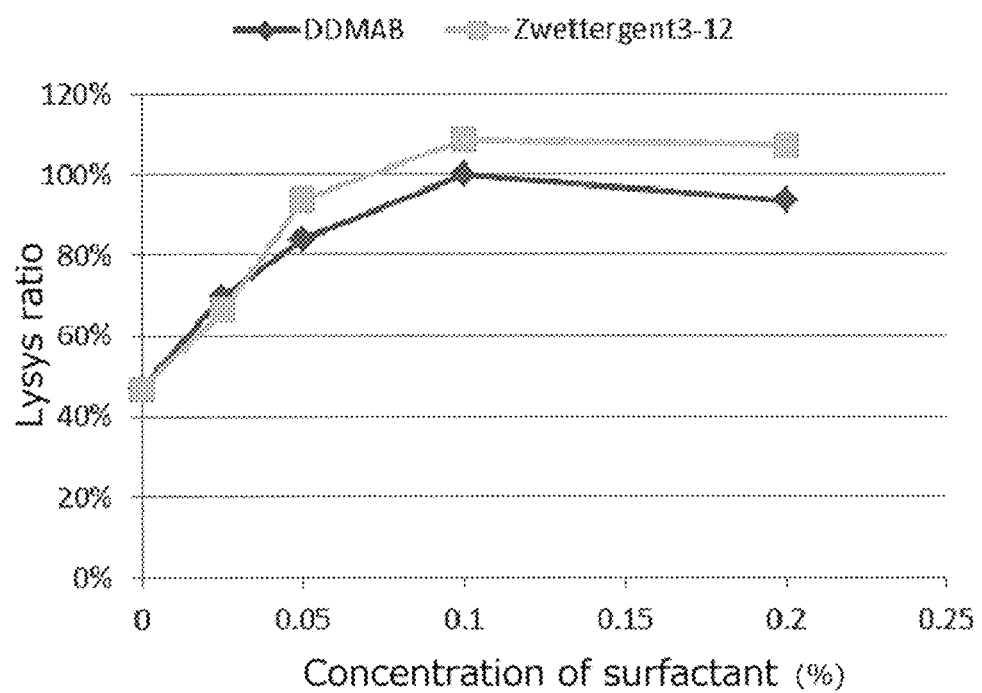

METHOD FOR DETECTING *STAPHYLOCOCCUS* CONTAINED IN MILK

CROSS-REFERENCE TO RELATED APPLICATIONS

This application is a Divisional of copending application Ser. No. 15/105,440, filed on Jun. 16, 2016, which is the National Phase under 35 U.S.C. § 371 of International Application No. PCT/JP2014/083459, filed on Dec. 17, 2014, which claims the benefit under 35 U.S.C. § 119(a) to Patent Application No. 2013-261823, filed in Japan on Dec. 18, 2013, all of which are hereby expressly incorporated by reference into the present application.

TECHNICAL FIELD

The present invention relates to a lysis method and detection method for detecting a *staphylococcus,* which is a causative bacterium of mastitis, in milk of livestock.

BACKGROUND ART

Milk of livestock animals, of which typical examples are cow, sheep, and goat, may not be sterile, and may be contaminated with certain microorganisms due to diseases or environment. In particular, it is known that animals with a disease caused by infection of a microorganism in the udder often discharge a lot of the microorganisms into milk. Typical diseases of livestock animals caused by infection of a microorganism include mastitis.

Mastitis is inflammation of the laticifer system or milk gland tissue, and it is caused largely by invasion, colonization, and proliferation of a microorganism in the udder. Although many kinds of animals contract mastitis, it is said that, especially concerning cow's mastitis in dairy cows, 15 to 40% of the whole dairy cows contract mastitis, and thus it is one of the extremely important diseases for dairy farmers. If a dairy cow contracts mastitis, not only the milk synthesis function is inhibited to result in reduction of lactation amount, or even stop of lactation as the case may be, but also enormous economical losses are imposed on dairy farmers, such as cost of medical treatment and penalty concerning milk price due to degradation of milk quality. Furthermore, it also increases the labor of dairy farmers, since, for example, milking of teats suffering from mastitis must be separately performed for preventing infection.

Mastitis is caused by infection of various microorganisms. Among the causative bacteria, staphylococci, especially *Staphylococcus aureus,* are known as causative bacteria of intractable mastitis, and it is also known that they are transmitted to other dairy cows via milking machines, and so forth.

As the method for detecting staphylococci in milk, cultivation-based methods are widely used. Since the cultivation-based methods require several days for obtaining a result, they are not suitable for quick identification of causative bacteria. In contrast, identification methods based on an antigen-antibody reaction using an antibody directed to an ingredient specific to a causative bacterium, especially the immunochromatographic method, can provide the result in several tens of minutes, and therefore they are widely used as quick and convenient inspection methods (for example, Patent document 1). The inventors of the present invention have examined use of an immunochromatographic method also as a method for detecting a substance contained in milk of livestock animals (Patent document 2).

In immunological measurement methods such as the immunochromatographic method, it is necessary to lyse bacterial cells to release antigens from the inside of the cells to the outside of the cells. As the method for lysing *Staphylococcus aureus* cells, there are known a method of using a lytic enzyme, lysostaphin (Patent documents 1 and 3), a method of using a treatment with a lytic enzyme and/or a bacteriocin having a bacteriolytic activity, a surfactant, and a protein denaturant (Patent document 4), and a method of using a treatment with a lysis reagent containing a lytic enzyme, a nonionic surfactant, and a chelating agent (Patent document 5). However, the aforementioned patent documents describe use of cultured cell suspension, and do not describe lysis effects in a high protein and high fat content solution such as milk.

PRIOR ART REFERENCES

Patent Documents

Patent document 1: Japanese Patent Unexamined Publication (KOKAI) No. 1-244370
Patent document 2: Japanese Patent Unexamined Publication (KOKAI) No. 2012-122921
Patent document 3: Japanese Patent Unexamined Publication (KOKAI) No. 11-28099
Patent document 4: International Patent Publication WO2005/064016
Patent document 5: Japanese Patent Unexamined Publication (KOKAI) No. 2006-246792

Non-Patent Documents

Non-patent document 1: Journal of Dairy Research (1997) 64 253-260

SUMMARY OF THE INVENTION

Object to be Achieved by the Invention

Mastitis is caused by infection of various microorganisms, and therefore antibiotics that exhibit efficacy against mastitis may differ depending on type of causative microorganism. Further, certain specific types of microorganisms have different characteristics, such as causing transmission to other teats or individuals, or require different post-infectious handling. Therefore, it is extremely important to quickly, conveniently, and highly sensitively identify the causative microorganism existing in milk. In particular, as for *Staphylococcus aureus,* which causes intractable mastitis, and is infectious, it is extremely important to find it in an early stage of infection for preventing expansion of damage of mastitis. However, in an early stage of infection, bacterial number of *Staphylococcus aureus* in milk may frequently very few, and therefore there is desired a method that enables quick and highly sensitive detection thereof.

The cultivation-based methods widely used as methods for detecting a bacterium have a problem that they require several days to obtain a result. In contrast, the immunological measurement methods based on an antigen-antibody reaction, such as the immunochromatographic method, have an advantage that they enable quick and convenient detection of causative bacteria, and thus enable early therapeutic treatment with an antibacterial agent.

In order to highly sensitively detect a specific substance in cells of a causative bacterium by an immunological measurement method, it is necessary to highly efficiently lyse the cells to release the antigen in the inside of the cells to the outside of the cells. However, when milk is used as a test sample, conventional techniques cannot provide sufficient lysis in many cases, because of the influences of proteins such as casein, milk fat globules, and so forth contained in milk in large amounts. It is also known that *Staphylococcus aureus* cells are adsorbed on milk fat globules contained in milk (Non-patent document 1), and it has been found that lysis ratio attainable by the usual techniques are easily further reduced by such a phenomenon. As described above, any effective lysis method for efficiently detecting staphylococci contained in milk was not known.

An object of the present invention is to provide a lysis method, lysis treatment solution, detection method using an immunochromatographic device, and detection kit comprising an immunochromatographic device for detecting whether causative bacterium of mastitis is a *staphylococcus* or not by using milk of a livestock animal.

Means for Achieving the Object

The inventors of the present invention considered that, in order to detect staphylococci in milk, it is necessary to highly efficiently extract target antigens in cells, found that by simultaneously using a lytic enzyme and a plurality of kinds of surfactants for highly efficiently lysing staphylococci contained in milk, lysis efficiency is improved, and staphylococci contained in milk can be highly sensitively detected, and accomplished the present invention.

The present invention thus provides the followings.

[1] A method for lysing a *staphylococcus*, which comprises the step of mixing a lysis agent containing a lytic enzyme and at least one kind of ampholytic surfactant with milk obtained form a livestock animal to lyse a *staphylococcus* existing in the milk.

[2] The method according to [1], wherein the lytic enzyme is lysostaphin.

[3] The method according to [1] or [2], wherein the lysis agent further contains at least one kind of nonionic surfactant.

[4] The method according to any one of [1] to [3], wherein the ampholytic surfactant is selected from the group consisting of a dimethylammoniopropanesulfonate, a dodecyldimethylammoniobutyrate, lauryl betaine, and amidopropyl betaine.

[5] The method according to any one of [1] to [4], wherein the nonionic surfactant is selected from the group consisting of a polyoxyethylene sorbitan fatty acid ester and a polyoxyethylene alkyl phenyl ether.

[6] A lysis agent for use in lysis of a *staphylococcus* contained in milk of a livestock animal, which contains a lytic enzyme and at least one kind of ampholytic surfactant.

[7] The lysis agent according to [6], which is for use in a method for diagnosing mastitis of a livestock animal.

[8] A method for detecting a *staphylococcus* contained in milk of a livestock animal, which comprises the method according to any one of [1] to [5], and further comprises the step of detecting a specific substance derived from the inside of cells of the *staphylococcus* and released by lysis.

[9] The method according to [8], wherein the step of detecting a specific substance is performed by an immunochromatographic method.

[10] The method according to [9], wherein the immunochromatographic method comprises:

(1) the step of contacting the milk containing the specific substance with a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a part existing upstream therefrom, and (2) the step of flowing the milk up to the second part or a part existing downstream therefrom to obtain a detectable signal of the label at the second part or a part existing downstream therefrom.

[11] The method according to [10], wherein the labeled first antibody directed to the specific substance is retained in the first part.

[12] The method according to [10] or [11], wherein the third part is constituted by two or more kinds of members having voids that can remove milk fat globules of different particle sizes, respectively.

[13] The method according to [12], wherein the third part is constituted by a first member disposed downstream and a second member disposed upstream, and retention particle size of the second member is larger than retention particle size of the first member.

[14] A kit for detecting a *staphylococcus* contained in milk of a livestock animal, which comprises the lysis agent according to [6] or [7], and an immunochromatographic device for detecting a specific substance contained in milk, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk.

The present invention also provides the followings.

[1] A method for lysing a *staphylococcus* contained in milk, which comprises:

the step of mixing a lysis agent containing lysostaphin, an ionic surfactant, and a nonionic surfactant with the milk to lyse a *staphylococcus* existing in the milk.

[2] The lysis method according to [1], wherein the ionic surfactant is an ampholytic surfactant.

[3] The lysis method according to [2], wherein the ampholytic surfactant is selected from a dimethylammoniopropanesulfonate, a dodecyldimethylammoniobutyrate, lauryl betaine, and amidopropyl betaine; and/or the nonionic surfactant is selected from a polyoxyethylene alkyl phenyl ether and a polyoxyethylene sorbitan fatty acid ester.

[4] The lysis method according to [2] or [3], wherein, in the step of mixing the lysis agent with the milk to lyse a *staphylococcus* existing in the milk, final concentration of the ampholytic surfactant is not lower than 0.03% and not higher than 0.2%.

[5] The lysis method according to [4], wherein, in the step of mixing the lysis agent with the milk to lyse a *staphylococcus* existing in the milk, final concentration of lysostaphin is not lower than 0.1 mg/µl and not higher than 200 mg/µl; and/or in the step of mixing the lysis agent with the milk to lyse a *staphylococcus* existing in the milk, final concentration of the nonionic surfactant is not lower than 0.03% and not higher than 10%.

[6] A method for detecting a *staphylococcus* contained in milk, which comprises:

the step of mixing the lysis agent with the milk to lyse a *staphylococcus* existing in the milk defined in any one of [1] to [5], and further comprises:

the step of detecting a specific substance derived from the inside of the *staphylococcus* and released by lysis.

[7] The detection method according to [6], which is performed by an immunochromatographic method.

[8] The detection method according to [7], wherein the immunochromatographic method comprises:

(1) the step of contacting the milk containing the specific substance with a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a part existing upstream therefrom, and (2) the step of flowing the milk up to the second part or a part existing downstream therefrom to obtain a detectable signal of the label at the second part or a part existing downstream therefrom.

[9] The detection method according to [8], wherein the labeled first antibody directed to the specific substance is retained in the first part.

[10] The detection method according to [8] or [9], wherein the third part is constituted by two or more kinds of members having voids that can remove milk fat globules of different particle sizes, respectively.

[11] The detection method according to [10], wherein the third part is constituted by a first member disposed downstream and a second member disposed upstream, and retention particle size of the second member is larger than retention particle size of the first member.

[12] The lysis agent defined in any one of [1] to [5].

[13] The lysis agent according to [12], which is for use in a method of diagnosing mastitis of a livestock animal.

[14] A kit for detecting a *staphylococcus* contained in milk, which comprises:

the lysis agent according to [12] or [13], and an immunochromatographic device for detecting a specific substance contained in milk, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk.

Effect of the Invention

According to the present invention, a *staphylococcus* contained in milk can be quickly, conveniently, and highly sensitively detected on the spot. In particular, in the case of diagnosis of cow's mastitis, if a visually recognizable label is used, the diagnosis can be performed in a dairy farm without using any apparatus etc., so that a causative bacterium can be quickly specified before further aggravation of pathological conditions, and appropriate treatment policies such as selection of a suitable antibiotics, and countermeasures for preventing expansion of infection can be determined at an early stage.

BRIEF DESCRIPTION OF THE DRAWINGS

FIG. 1 shows effect of an ampholytic surfactant in the presence of a lytic enzyme and a nonionic surfactant in detection of *Staphylococcus aureus* by enzyme immunoassay (ELISA).

FIG. 2 shows a schematic sectional view of the test strip of the immunochromatographic device used in Example 2, which comprises a labeled antibody-impregnated member 1 (first part), a membrane carrier 2 for chromatographic development (second part), a part 3 for capturing, a member 4 serving as both a member for sample addition and a member for removal of fat globules (third part), a member 5 for absorption, a substrate 6, and a member 7 for removal of fat globules (third part).

FIG. 3 shows effect of an ampholytic surfactant in the presence of a lytic enzyme and a nonionic surfactant in detection of *Staphylococcus aureus* by an immunochromatographic method.

MODES FOR CARRYING OUT THE INVENTION

Hereafter, the present invention will be explained in more detail. In the present invention, when a numerical value range is represented as "X to Y", the range includes the values X and Y as the minimum and maximum values. The symbol "%" is used for indicating percent on mass basis, unless especially indicated. The expression "A and/or B" means at least one of A and B, including the cases of referring to only A, only B, and A and B.

The present invention provides a lysis agent for lysing bacteria contained in milk. The lysis agent of the present invention contains a lytic enzyme and a specific surfactant.

[Lytic Enzyme]

Type of the lytic enzyme used in the present invention is not particularly limited, and arbitrary two or more kinds of lytic enzymes may also be used in combination, as required. As for the causative bacterium of mastitis, infection by *Escherichia coli, Klebsiella* bacterium, or *Staphylococcus aureus* frequently occurs, and therefore it is also preferable to use one or two or more kinds of lytic enzymes that can exhibit bacteriolytic action to these microorganisms in combination. For example, one or two or more kinds of lytic enzymes selected from lysozyme, lysostaphin, pepsin, glucosidase, galactosidase, achromopeptidase, β-N-acetylglucosaminidase, and so forth can be used. For example, there has been proposed a method of using lysozyme as a lytic enzyme and a cell membrane lysing agent (Japanese Patent Unexamined Publication (KOKAI) No. 63-167799).

When presence of a *staphylococcus* is especially suspected as the causative bacterium of mastitis, it may be preferable to use lysostaphin, which specifically exhibits a bacteriolytic action against staphylococci, alone or in combination with another lytic enzyme. A method for lysing *Staphylococcus aureus* with lysostaphin is disclosed in Japanese Patent Unexamined Publication (KOKAI) No. 11-28099, and those skilled in the art can easily obtain lysostaphin as a lytic enzyme. The entire disclosures of the aforementioned patent publication are incorporated into the disclosures of this specification by reference.

The naturally occurring type lysostaphin is a zinc protease produced by *Staphylococcus simulans*, and it is known that it lyses *Staphylococcus aureus* or other bacteria of the same genus by hydrolyzing glycylglycine bonds in glycopeptide chains of the cell wall peptidoglycan thereof. In this specification, the term lysostaphin also means, besides the aforementioned naturally occurring type lysostaphin, a variant lysostaphin having the amino acid sequence of the naturally occurring type lysostaphin, but including a mutation such as addition, deletion, and/or substitution of one or more amino acid residues within such an extent that the aforementioned hydrolysis activity is maintained. The lysostaphin may also be a modified lysostaphin consisting of the naturally occurring type lysostaphin or variant lysostaphin to which another compound such as saccharide and polyethylene glycol is bound within such an extent that the hydrolysis activity is maintained. These lysostaphins can be obtained by the culture method described in Japanese Patent Unexamined Publication (KOKAI) No. 11-28099, or a genetic engineering technique, or by purchasing a marketed product.

Content of the lytic enzyme in the lysis agent (when two or more kinds of lytic enzymes are used, it is the content as the total amount of the lytic enzymes) is not particularly limited so long as a lysis ratio effective for the detection is secured. However, as for the lower limit of the content, when an enzyme agent (or enzyme protein) having an activity of 3500 units/mg or higher is used, the content can be determined so that the final concentration of the enzyme agent (or enzyme protein) in the mixture with milk becomes 0.03 μg/ml or higher, preferably 0.15 μg/ml or higher, more preferably 0.3 μg/ml or higher, further preferably 1.5 μg/ml or higher, particularly preferably 1 μg/ml or higher. As for the upper limit of the content of the lytic enzyme, the content can be determined from the economical point of view, or the like, as required, and irrespective of how the lower limit is defined, it can be 200 μg/ml or lower, preferably 100 μg/ml or lower, more preferably 75 μg/ml or lower, further preferably 50 μg/ml or lower, particularly preferably 25 μg/ml or lower. In terms of the enzymatic activity, the lower limit of the content, the content can be determined so that the final concentration thereof in the mixture with milk should become 0.105 unit/ml or higher, preferably 0.525 unit/ml or higher, more preferably 1.05 units/ml or higher, further preferably 5.25 units/ml or higher, particularly preferably 10.5 units/ml or higher. As for the upper limit, the content can be determined to be 700 units/ml or lower, preferably 350 units/ml or lower, more preferably 262.5 units/ml or lower, further preferably 175 units/ml or lower, particularly preferably 87.5 units/ml or lower, irrespective of how the lower limit is defined. The enzymatic activity referred to in this specification is defined as follows.

Definition of enzymatic activity: One unit is defined to be an enzyme amount that reduces turbidity of a suspension of a heat-treated objective bacterium (preferably *Staphylococcus aureus*, more preferably *Staphylococcus aureus* 8325-4) as a substrate by 0.01 OD at 600 nm in 1 minute at 25° C. and pH 8.0 (in 1.0 mL of 0.2 mol/L Tris buffer, pH 8.0, 25° C., initial turbidity is 1.0).

[Surfactant]

A surfactant that ionizes and becomes an ion, when it is dissolved in water, is referred to as ionic surfactant, and a surfactant that does not become an ion is referred to as non-ionic (nonionic) surfactant. Ionic surfactant is further classified into anionic surfactant, cationic surfactant, and ampholytic surfactant.

In the present invention, together with the lytic enzyme, at least one kind of ampholytic surfactant, at least one kind of anionic surfactant, or at least one kind of cationic surfactant, or a combination of any of these is used. It is preferable to use at least one kind of ampholytic surfactant, or at least one kind of nonionic surfactant, or a combination of these, together with the lytic enzyme. It is more preferable to use at least one kind of ampholytic surfactant, and at least one kind of nonionic surfactant in combination, together with the lytic enzyme.

Examples of the ampholytic surfactant include those of amino acid type (alkylaminofatty acid salts), betaine type (alkyl betaines), amine oxide type (alkylamine oxides), and so forth, but it is not particularly limited. More specific examples include dimethylammoniopropanesulfonates, dodecyldimethylammoniobutyrates, lauryl betaine, and amidopropyl betaine. Further specific examples include n-tetradecyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, n-hexadecyl-N,N-dimethyl-3-ammonio-1-propanesulfonate, and N-dodecyl-N,N-(dimethylammonio)butyrate.

Content of the ampholytic surfactant in the lysis agent (when two or more kinds of ampholytic surfactants are used, it is the content as the total amount of the ampholytic surfactants) is not particularly limited, so long as a lysis ratio effective for the detection is secured. However, as for the lower limit, it can be determined so that the final concentration thereof in the mixture with milk becomes 0.03% or higher, preferably 0.05% or higher, more preferably 0.06% or higher, further preferably 0.07% or higher, particularly preferably 0.08% or higher, irrespective of the content of the lytic enzyme. As for the upper limit of the content of the ampholytic surfactant, the content can be determined so that the reaction catalyzed by the lytic enzyme and antigen-antibody reactions are not significantly inhibited. In any case, it can be 1% or lower, preferably 0.75% or lower, more preferably 0.5% or lower, further preferably 0.3% or lower, particularly preferably 0.2% or lower.

As the nonionic surfactant, any of those of ester ether type, ester type, and ether type can be preferably used. More specifically, examples include polyoxyethylene alkyl ethers, polyoxyethylene alkyl phenyl ethers, fatty acid sorbitan esters, alkyl polyglucosides, fatty acid diethanolamides, alkyl monoglyceryl ethers, polysorbates (formed by condensation of several tens of molecules of ethylene oxide to a fatty acid sorbitan ester), and so forth, but it is not particularly limited. Especially preferred examples include polysorbates, more specifically, polyoxyethylene (20) sorbitan monolaurate, polyoxyethylene (60) sorbitan monostearate, polyoxyethylene (65) sorbitan tristearate, and polyoxyethylene (80) sorbitan monooleate, and so forth, as well as polyoxyethylene alkyl phenyl ethers, more specifically, polyoxyethylene (10) octyl phenyl ether, and so forth.

Content of the nonionic surfactant in the lysis agent (when two or more kinds of nonionic surfactants are used, it is the content as the total amount of the nonionic surfactants) is not particularly limited so long as, for example, when an immunochromatographic method is used, flow of a developing solution is secured. However, in any case, as for the lower limit thereof, the content can be determined so that the final concentration of the nonionic surfactant in the mixture with milk becomes 0.03% or higher, preferably 0.05% or higher, more preferably 0.075% or higher, further preferably 0.1% or higher, particularly preferably 0.3% or higher. As for the upper limit of the content of the nonionic surfactant, the content can be determined so that the reaction catalyzed by the lytic enzyme and antigen-antibody reactions are not significantly inhibited, and in any case, it can be 10% or lower, preferably 7.5% or lower, more preferably 5.0% or lower, still more preferably 3% or lower, particularly preferably 2% or lower.

As the anionic surfactant, any of carboxylic acid salts, sulfonic acid salts, sulfuric acid ester salts, and so forth can be preferably used. More specific examples include alkyl ether carboxylates, linear alkylbenzenesulfonates (LAS), α-olefinsulfonates (AOS), dialkylsulfosuccinates, formaldehyde condensates of naphthalenesulfonate, alkyl sulfuric acid ester salts (AS), polyoxyethylenealkylsulfuric acid ester salts (AES) obtained by addition of ethylene oxide to a higher alcohol and following sulfation, phosphoric acid ester salts of a higher alcohol or ethylene oxide adduct thereof, and so forth. Further specific examples include sodium alkylsulfates such as sodium dodecylsulfate and sodium myristylsulfate, sodium N-acylsarcosinates such as sodium N-lauroylsarcosinate and sodium N-myristoylsarcosinate, sodium dodecylbenzenesulfonate, hydrogenated coconut fatty acid monoglyceride monosodium sulfate, sodium laurylsulfoacetate, N-acylglutamates such as sodium N-palmitoylglutamate, N-methyl-N-acylalanine sodium, and sodium α-olefinsulfonates.

As the cationic surfactant, any of those of amine salt type and quaternary ammonium salt type can be preferably used. More specific examples include distearyldimethylbenzylammonium chloride, benzalkonium chloride, hexadecyltrimethylammonium bromide, hexadecyltrimethylammonium bromide, myristyltrimethylammonium bromide, and so forth.

[Example of Composition]

In one of the most preferred embodiments, the lysis agent comprises lysostaphin, an ampholytic surfactant, and a nonionic surfactant. For the lysis agent containing lysostaphin, an ampholytic surfactant, and a nonionic surfactant, preferred ampholytic surfactant is one selected from a dimethylammoniopropanesulfonate, a dodecyldimethylammoniobutyrate, lauryl betaine and amidopropyl betaine; preferred nonionic surfactant is a polyoxyethylene alkyl phenyl ether or a polyoxyethylene sorbitan fatty acid ester. Concentrations of such ingredients of the lysis agent can be determined so that, in the step of lysing bacteria existing in milk by mixing the lysis agent with the milk, the final concentration of lysostaphin is not lower than 0.1 mg/μl and not higher than 200 mg/μl, the final concentration of the ampholytic surfactant is not lower than 0.03% and not higher than 0.2%, and the final concentration of the nonionic surfactant is not lower than 0.03% and not higher than 10%.

[Other Ingredients]

The lysis agent of the present invention may contain, besides the lytic enzyme and the surfactant, one or more kinds of other ingredients, so long as the intended effect is not markedly degraded. Preferred examples of the ingredients other than the lytic enzyme and the surfactant include a substance that has an effect of promoting the lysis. Specific examples include glutaraldehyde, halogen compounds, chlorhexidine, alcohols (for example, methanol, ethanol, 1-propanol, 2-propanol, 1-butanol, 2-butanol, 2-methyl-1-propanol, 2-methyl-2-propanol), phenol, hydrogen peroxide, acrinol, guanidine and salt thereof, chelating agents, organic acids and salts thereof, polyhydric alcohols (for example, ethylene glycol, propylene glycol, diethylene glycol, and glycerin), and reducing agents such as 2-mercaptoethanol, dithiothreitol, cystine, and thiophenol, but they are not limited to these.

[Lysis Conditions and Lysis Ratio]

In the present invention, the lysis agent can be used by mixing it with milk. Mixing ratio of milk and the lysis agent is not particularly limited, so long as the final concentrations of the lytic enzyme etc. are properly maintained, and sufficient lysis ratio can be secured. If the lysis agent is used in a volume relatively small with respect to milk, the milk is not diluted. Therefore, it can be expected that cells can be detected with higher sensitivity. When the lysis agent is used in a volume relatively large with respect to milk, influences of fat globules and proteins contained in milk are reduced, and therefore it can be expected that cells can be detected in a shorter time. From the viewpoint that a higher ratio of milk in the mixture of milk and the lysis agent (milk/(milk+lysis agent)×100) can provide higher detection sensitivity, the ratio can be, for example, 5% or higher, preferably 10% or higher, more preferably 20% or higher, further preferably 30% or higher, irrespective of the other conditions. As for the upper limit of the ratio, if the lysis agent solidified by drying or the like is used, the ratio of milk can be made to be 100%, irrespective of the other conditions. The ratio of the milk can be 90% or lower, 80% or lower, 70% or lower, 60% or lower, or 50% or lower, irrespective of the other conditions. As for the upper limit, the ratio may be determined in consideration of ease of mixing, stability of the lysis agent as a solution, and so forth.

In the present invention, it is sufficient to simply mix milk with the lysis agent. Temperature at the time of mixing, and treatment time for allowing the enzyme to act following the mixing are not particularly limited, so long as the lytic enzyme used can exhibit the activity, and the temperature may usually be room temperature. The treatment time for allowing the reaction after the mixing can be appropriately determined by those skilled in the art in consideration of lysis ratio. In the present invention, since combination and concentrations of lytic enzyme and surfactant appropriate for staphylococci are used, the treatment time can be markedly shortened compared with a case where only a lytic enzyme is used. In the present invention, the treatment time is generally about several tens of minutes to several hours, and more specifically, it can be 120 minutes or shorter, preferably 60 minutes or shorter, more preferably 45 minutes or shorter, further preferably 25 minutes or shorter, still further preferably 20 minutes or shorter, still more further preferably 15 minutes or shorter. The treatment time can also be made to be substantially 0 (after milk and the lysis agent are mixed, the mixture is immediately subjected to the measurement). According to the present invention, even by the treatment for such a short time, a lysis ratio of 90% or higher is secured, and *staphylococcus* can be detected with high sensitivity.

According to the investigations of the inventors of the present invention, it could be confirmed that, with the conditions described in the examples of this specification, a lysis ratio of 100% can be attained by treating milk containing about $5 \times 10^8$ cells/ml of *Staphylococcus aureus* with the lysis agent of the present invention for about 30 minutes. As for the basis of the lysis ratio, lysis ratio observed for a suspension of a target *staphylococcus* subjected to a preliminary treatment with a nonionic surfactant of a proper concentration, and then further subjected to ultrasonication, and a sufficient enzyme treatment, as required, can be defined as 100%.

[Detection Means]

Staphylococci lysed according to the present invention can be detected by various kinds of immunological methods using an ingredient of bacterial cells as an antigen. Examples of immunological measurement method include, for example, immunochromatographic method, agglutination reaction method, enzyme immunoassay (ELISA), radioimmunoassay (RIA), fluoroimmunoassay (FIA), and so forth, but it is not limited to these. At the time of performing the immunological methods, a substance for blocking for preventing non-specific adsorption, or a substance for preventing cross-reaction with bacteria other than the target bacterium may be used.

When an immunochromatographic method is used, it can be carried out typically as follows.

[Immunochromatographic Method and Immunochromatographic Device]

An antigen-antibody reaction can be detected by the sandwich assay using a "labeled first antibody directed to a specific substance" retained by a first part, and a "second antibody directed to the specific substance" immobilized on a second part. Alternatively, an antigen-antibody reaction may also be detected by the competition method using a labeled specific substance retained by a first part, and an antibody directed to the specific substance immobilized on a second part. However, in the present invention, the sandwich assay method is preferred, since it shows high detection sensitivity and gives a line indicating detection of antibody as a positive result.

The immunochromatographic device is a device for detecting a specific substance contained in milk by an immunochromatographic method, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk. As a specific example of the structure of the test strip, that of the test strip of which schematic sectional view is shown in FIG. 2 can be mentioned. In FIG. 2, a member 7 for removal of fat globules (third part) is disposed downstream from a member 4 for sample addition, and upstream from a labeled antibody-impregnated member (first part) 1.

The immunochromatographic device can be produced in a known manner by using marketed materials.

The material used for the first part is not particularly limited, so long as a material enabling immunochromatography is chosen, but preferred examples include a fiber matrix of cellulose derivative etc., filter paper, glass fiber, cloth, cotton, and so forth.

The material used for the second part is not particularly limited, so long as a material enabling immunochromatography is chosen, but preferred examples include cellulose nitrate, mixed cellulose nitrate ester, polyvinylidene fluoride, nylon, and so forth.

The material used for the third part preferably has voids that enable removal of milk fat globules contained in milk and having a diameter of about 1 to ten and several micrometers. The third part must be disposed upstream from the aforementioned second part consisting of a porous membrane having a pore diameter of several tens to several hundreds nm, and is preferably disposed upstream from the aforementioned first part, i.e., at a position at which a sample solution first contacts with and passes through the test strip.

The voids of the third part may have a size that enables removal of milk fat globules, and retention particle size is preferably 0.1 to 10 µm, more preferably 1 to 3.5 µm. The material is not particularly limited, so long as a material having voids showing a retention particle size within the aforementioned range is chosen, but preferred examples include a matrix of fibers such as cellulose derivatives, filter paper, glass fiber, cloth, cotton, and so forth. The retention particle size means such a particle size of milk fat globules that milk fat globules having a particle size not smaller than the retention particle size cannot pass through the voids and are retained by the third part, and substantially corresponds to average pore size of the voids of the third part, and 50% or more, preferably 60% or more, more preferably 70% or more, still more preferably 80% or more, particularly preferably 90% or more, most preferably 98% or more, of milk fat globules having a particle size not smaller than the retention particle size cannot pass through the voids and are retained by the third part. Ratio of milk fat globules to be retained can be measured by a method well known to those skilled in the art. For example, the catalogue of GF/B provided by GE Healthcare Bioscience describes that the retention particle size (particle diameter for which retention efficiency is 98%, the term retention particle size used in this specification has this meaning, unless especially indicated) thereof is 1.0 µm, and such a particle size as mentioned above can be confirmed by a method well known to those skilled in the art.

The aforementioned third part may consist of a single kind of material having a specific retention particle size, or may consist of a laminate comprising materials having different retention particle sizes and integrally adhered so that the retention particle size becomes smaller stepwise, in order to increase milk fat globule separation efficiency. Such a third part as mentioned above constituted by two or more kinds of members that can remove milk fat globules of different particle sizes constitutes a preferred embodiment of the present invention, and in a more preferred embodiment of the present invention, the third part is constituted with a first member disposed downstream and a second member disposed upstream, and the retention particle size of the second member is larger than the retention particle size of the first member. When the third part is constituted with such two kinds of members, it is preferred that the retention particle size of the first member disposed downstream is 1.0 to 2.0 µm, and the retention particle size of the second member disposed upstream is 3.0 to 3.5 µm. In order to highly sensitively detect a specific substance from milk containing milk fat globules of high concentration and wide particle size distribution, especially such milk not diluted after milking, it is preferred that the third part is constituted with a combination of a member having a small retention particle size and a member having a large retention particle size.

The aforementioned first part retains a labeled first antibody directed to a specific substance, or a labeled specific substance. If the first part retains a labeled first antibody directed to a specific substance, the specific substance can be detected by the sandwich assay method. If the first part retains a labeled specific substance, the specific substance can be detected by the competition method. Since the sandwich assay method that shows high detection sensitivity and gives a line indicating detection of antibody as a positive result is more preferred for the present invention, the first part preferably retains a labeled first antibody directed to a specific substance.

When the first part is made to retain a labeled first antibody directed to a specific substance, two kinds of antibodies, the first antibody directed to the specific substance, and a second antibody also directed to the specific substance, are used. In order to enable detection of the specific substance by the sandwich assay method, the aforementioned first antibody and second antibody are antibodies that can simultaneously bind to the specific substance, and it is preferred that the epitope of the specific substance to be recognized by the aforementioned first antibody is different from the epitope of the specific substance to be recognized by the aforementioned second antibody.

In the present invention, in order to obtain a detectable signal, the first antibody or the specific substance retained by the first part is labeled. Examples of the label used for the present invention include a colored particle, enzyme, radioisotope, and so forth, and it is preferable to use a colored particle that can be visually detected without any special equipment. Examples of the colored particle include metal microparticles such as those of gold and platinum, nonmetallic particles, latex particles, and so forth, but are not limited to these. The colored particle may have any size so long as the colored particle has such a size that it can be transported downstream through the inside of the voids of the test strip, but it preferably has a size of 1 nm to 10 μm, more preferably 5 nm to 1 μm, still more preferably 10 to 100 nm, in diameter.

[Object of Detection]

According to the present invention, a *staphylococcus* contained in milk can be detected. The term "*staphylococcus*" used in the present invention refers to a bacterium belonging to the genus *Staphylococcus*, unless especially indicated, and bacteria belonging to the genus *Staphylococcus* include *Staphylococcus aureus*, the other bacteria of the genus *Staphylococcus*, and CNS (Coagulase Negative *Staphylococcus*). The CNS bacteria include *Staphylococcus intermedius*, *Staphylococcus hyicus*, *Staphylococcus xylosus*, *Staphylococcus epidermidis*, and so forth. According to the present invention, staphylococci contained in milk obtained from a livestock animal such as cow as it is, which contains fat globules and proteins of high concentration, can be detected by using the lysis agent containing appropriately formulated lytic enzyme and surfactant.

The specific substance measured in the present invention may be any substance so long as it is a substance that can be measured by an immunological method such as immunochromatographic method, but it is preferably a component of a bacterium or a substance that is secreted by a bacterium. The specific substance is more preferably the L7/L12 ribosomal protein of a bacterium. High detection sensitivity can be obtained for the L7/L12 ribosomal protein, since it exists in cells in a large copy number.

[Antibody]

The antibody used in the present invention can be prepared by the method described in International Patent Publication WO00/06603. When the bacterial ribosomal protein L7/L12 is used as the antigen, the antibody can be prepared by using a full length protein or a partial peptide of the bacterial ribosomal protein L7/L12 as an antigen, but it is preferably prepared by using the full length protein as an antigen. An antiserum containing an antibody (polyclonal antibody) that recognizes the L7/L12 ribosomal protein can be obtained by inoculating such a partial peptide or full length protein as mentioned above as it is or crosslinked with a carrier protein to an animal, together with an adjuvant as required, and collecting the serum of the animal. Further, the antibody purified from the antiserum can also be used. Examples of the animal used for the inoculation include sheep, horse, goat, rabbit, mouse, rat, and so forth, and sheep, rabbit, and so forth are especially preferred for preparing polyclonal antibodies. Further, it is more preferable to use, as the antibody, a monoclonal antibody obtained by a known method in which a hybridoma cell is prepared, and in such a case, mouse is preferred as the animal. If, as such a monoclonal antibody, a monoclonal antibody that reacts with the ribosomal protein L7/L12 of a specific bacterium that causes mastitis, but does not react with the ribosomal protein L7/L12 of a bacterium that causes mastitis other than the above specific bacterium is retrieved by screening, it can be utilized for diagnosing whether an animal suffers from infection by the bacterium or not.

A monoclonal antibody that recognizes a substance other than the ribosomal protein L7/L12 as an antigen may also be used, so long as the antibody is a monoclonal antibody that reacts with a component of a specific bacterium that causes mastitis or a substance secreted by such a bacterium, but does not react with a component of a bacterium that causes mastitis other than the foregoing specific bacterium or a substance secreted by such a bacterium.

Further, as the monoclonal antibody, it is preferable to use a monoclonal antibody of which antigen-antibody reaction is not inhibited by any contaminants other than the specific substance contained in milk. For example, milk contains a large amount of proteins such as casein, and they may inhibit the reaction of the specific substance and the monoclonal antibody. When a monoclonal antibody directed to the specific substance is prepared in a conventional manner, for example, a monoclonal antibody of which antigen-antibody reaction is not inhibited by casein or the like, or a monoclonal antibody of which antigen-antibody reaction is hardly affected by casein or the like may be preferably chosen and used. Such a monoclonal antibody can be easily obtained by preparing monoclonal antibodies that specifically react with an antigen in a usual manner, and then selecting a monoclonal antibody of which antigen-antibody reaction is not substantially inhibited by a contaminant such as casein by examining whether the antigen-antibody reaction is inhibited or not in the presence of the contaminant.

[Others]

In the present invention, the test strip described above may be used as it is as an immunochromatographic device, or the test strip may be stored in a case to constitute an immunochromatographic device. In the former case, if a large volume of milk is used as a sample, the immunochromatographic device is preferably used by directly immersing one end of the test strip into the sample contained in a container. In the latter case, if the volume of milk as a sample is small, the immunochromatographic device is preferably used by measuring a predetermined volume of the sample with a pipette or the like, and dropping the sample to the test strip. In the latter case, the case may have any shape so long as the test strip can be stored. The case may be formed with any material, and preferred examples include polypropylene, polycarbonate, and so forth.

The immunochromatographic device of the present invention can also be provided as a kit comprising a container such as microtube, and an additive solution, for example, an additive solution containing a lytic enzyme or surfactant for lysing the bacterium to elute the ribosomal protein L7/L12 into the solution.

EXAMPLES

Example 1

Effect of Ampholytic Surfactant in the Presence of Lytic Enzyme and Nonionic Surfactant in Detection of *Staphylococcus aureus* by Enzyme Immunoassay (ELISA)

(a) Preparation of Monoclonal Antibody Directed to Ribosomal Protein L7/L12

As the antibody to be labeled with gold colloid, *Staphylococcus aureus* ribosomal protein L7/L12 monoclonal antibody was used. According to the method described in International Patent Publication WO00/06603, Example 5, the *Staphylococcus aureus* L7/L12 ribosomal protein was obtained, and monoclonal antibodies were prepared by using this protein. Among the monoclonal antibodies, a combination of two kinds of monoclonal antibodies (SA-1 and SA-2) that can simultaneously bind to different sites of the aforementioned L7/L12 ribosomal protein was selected.

(b) Confirmation of Effect of Lytic Enzyme in ELISA

Effect of the lytic enzyme was confirmed as follows.

The monoclonal antibody SA-1 (10 μg/ml) and PBS (100 μl) were put into each well of a 96-well ELISA plate (Maxsorp ELISA Plate, Nunc), and adsorption of the antibody was allowed overnight at 4° C. After the supernatant was removed, a 1% bovine serum albumin solution (in PBS, 200 μl) was added, and the reaction was allowed at room temperature for 1 hour to attain blocking. After the supernatant was removed, each well was washed several times with a washing solution (0.02% Tween 20, PBS). *Staphylococcus aureus* suspended in marketed milk (about $5 \times 10^8$ cells/ml) was treated with each of the solutions mentioned in Table 1 for 30 minutes, and diluted 100 times with the same milk, the diluted suspension (100 μl) was added to each well, and the reaction was allowed at room temperature for 1 hour. Further, after the supernatant was removed, the monoclonal antibody SA-2 labeled with peroxidase and diluted with 0.02% Tween 20 in PBS to a final concentration of 1 μg/ml (100 μl) was added, and the reaction was allowed at room temperature for 1 hour. After the supernatant was removed, each well was further washed several times with the washing solution, then a TMB solution (KPL, 100 μl) was added to each well, and the reaction was allowed at room temperature for 10 minutes. Then, 1 mol/l hydrochloric acid (100 μl) was added to terminate the reaction, and absorbance was measured at 450 nm.

A cell suspension of the aforementioned *Staphylococcus aureus* containing Triton X-100 at a final concentration of 1.0% was preliminarily stirred overnight, and ultrasonicated (output 10, 1 minute×10 times). This suspension was subjected to a lysis treatment at 37° C. for 60 minutes with 10 μg/ml (35 units/ml) of lysostaphin (Wako Pure Chemical Industries, 3500 unit/mg, the same shall apply to the following examples unless especially indicated), and the lysis ratio observed in this suspension was defined to be 100%. The lysis ratio relative to the above lysis ratio was calculated for each condition.

The results are shown in FIG. 1. It was revealed that, in the case of the condition 1, in which ampholytic surfactant was not added, the lysis ratio was 55%, whereas when the ampholytic surfactant was added, the lysis ratio increased with all the conditions of adding the ampholytic surfactant, compared with the case where ampholytic surfactant was not added. Further, it was also revealed that, in the cases of the conditions 0 to 12, in which a different type of ampholytic surfactant was used, the lysis ratio similarly increased.

TABLE 1

| Condition | Lysostaphin, Wako Pure Chemical Industries (final concentration, μg/ml) | Surfactant | | | |
|---|---|---|---|---|---|
| | | Nonionic surfactant (trade name) | Final concentration (%) | Ampholytic surfactant (trade name) | Final concentration (%) |
| 1 | 10 | Polyoxyethylene sorbitan fatty acid ester (Tween 20) | 1 | None | — |
| 2 | 10 | | 1 | n-Tetradecyl-N,N-dimethyl-3-ammonio-1-propanesulfonate (Zwittergent 3-8, Calbiochem) | 0.1 |
| 3 | 10 | | 1 | n-Decyl-N,N-dimethyl-3-ammonio-1-propanesulfonate (Zwittergent 3-10, Calbiochem) | 0.1 |
| 4 | 10 | | 1 | n-Dodecyl-N,N-dimethyl-3-ammonio-1-propanesulfonate (Zwittergent 3-12, Calbiochem) | 0.1 |
| 5 | 10 | | 1 | n-Tetradecyl-N,N-dimethyl-3-ammonio-1-propanesulfonate (Zwittergent 3-14, Calbiochem) | 0.1 |
| 6 | 10 | | 1 | n-Hexadecyl-N,N-dimethyl-3-ammonio-1-propanesulfonate (Zwittergent 3-16, Calbiochem) | 0.1 |
| 7 | 10 | | 1 | n-Dodecyl-N,N-(dimethylammonio)butyrate (DDMAB, Calbiochem) | 0.1 |
| 8 | 10 | | 1 | Amidopropyl betaine (Enagicol L-30B, Lion) | 0.1 |
| 9 | 10 | | 1 | Lauryl betaine (Amphitol 24B, Kao) | 0.1 |
| 10 | 10 | Polyoxyethylene alkyl phenyl ether (Triton X-100) | 1 | n-Decyl-N,N-dimethyl-3-ammonio-1-propanesulfonate (Zwittergent 3-10, Calbiochem) | 0.1 |
| 11 | 10 | | 1 | n-Dodecyl-N,N-dimethyl-3-ammonio-1-propanesulfonate (Zwittergent 3-12, Calbiochem) | 0.1 |
| 12 | 10 | | 1 | n-Tetradecyl-N,N-dimethyl-3-ammonio-1-propanesulfonate (Zwittergent 3-14, Calbiochem) | 0.1 |

Example 2

Effect of Ampholytic Surfactant in the Presence of Lytic Enzyme and Nonionic Surfactant in Detection of *Staphylococcus aureus* by Immunochromatographic Method (1) Preparation of Immunochromatographic Device An immunochromatographic device was prepared as follows.

(a) Gold Colloid-labeled Antibody-impregnated Member

A gold colloid solution (particle size 60 nm, 0.9 mL, BB International) was mixed with 0.1 M potassium phosphate, pH 7.0, the monoclonal antibody SA-2 (100 µg/mL) to be labeled with gold colloid was added to the mixture, and the resulting mixture was left standing at room temperature for 10 minutes so that the antibody bound to the gold colloid particle surfaces. Then, a 10% aqueous solution of bovine serum albumin (BSA) was added at a final concentration of 1% in the gold colloid solution, so that the remaining surfaces of the gold colloid particles were blocked with BSA, to prepare a solution of the monoclonal antibody SA-2 labeled with gold colloid (henceforth referred to as "gold colloid-labeled antibody"). This solution was centrifuged (at 15000 rpm for 5 minutes) to precipitate the gold colloid-labeled antibody, and the supernatant was removed to obtain the gold colloid-labeled antibody. This gold colloid-labeled antibody was suspended in 20 mM Tris-hydrochloric acid buffer (pH 8.2) containing 0.25% BSA, 2.5% sucrose, and 35 mM NaCl to obtain a gold colloid-labeled antibody solution. A glass fiber pad of a strip-like shape (10 mm×300 mm) was impregnated with the gold colloid-labeled antibody solution (2 mL), and dried at room temperature under reduced pressure to obtain a gold colloid-labeled antibody-impregnated member 1 (first part).

(b) Part for Capturing Complex of Antigen and Gold Colloid-labeled Antibody

A nitrocellulose membrane having a width of 25 mm and a length of 300 mm was prepared as a membrane carrier 2 for chromatographic development with chromatography medium (second part).

A solution containing the monoclonal antibody SA-1 (1.5 mg/mL) was applied in the shape of a line in a volume of 1 µL/cm to the membrane carrier 2 for chromatographic development at a position of 10 mm from the end on the side of the chromatography development starting point, and dried at 50° C. for 30 minutes, and then the membrane carrier was immersed in a 0.5% sucrose solution for 30 minutes, and dried overnight at room temperature to obtain a part 3 for capturing the complex of the *Staphylococcus aureus* ribosomal protein L7/L12 antigen and the gold colloid-labeled antibody.

(c) Preparation of Immunochromatographic Device

A sectional view of immunochromatographic device is shown in FIG. 2. In addition to the aforementioned labeled antibody-impregnated member 1 and membrane carrier 2 for chromatographic development, 25 mm GF/DVA (filter member 4 having a thickness of 776 µm and consisting of glass fibers, retention particle size 3.5 µm, GE Healthcare Bioscience) and 20 mm GF/AVA (filter member 7 having a thickness of 299 µm and consisting of glass fibers, retention particle size 1.7 µm, GE Healthcare Bioscience) were adhered to each other as a member serving as both the member for sample addition and the member for removal of fat globules (third part), and filter paper as the member 5 for absorption was further prepared. After these members were adhered on a substrate 6 (thickness 254 µm, made of polystyrene, having adhesive for adhering the members), they were cut in a width of 5 mm to prepare the immunochromatographic device.

(2) Test

Measurement for cow's milk using the immunochromatographic device was performed as follows.

Milk (100 µl) containing *Staphylococcus aureus* at a final concentration of $1 \times 10^5$ (cfu/ml) was put into a microtube, 150 µl of a lysis treatment solution (1% (final concentration) of Tween 20, 10 µg/ml (35 units/ml) of lysostaphin, 0.1 M MOPSO, pH 7.5, different concentration of Zwettergent 3-12 or DDMAB) was added to the milk and mixed therein, and the treatment was performed at room temperature for 30 minutes. As the cow's milk, marketed milk for drinking was used. The aforementioned immunochromatographic device was immersed into the above mixed solution from the member 4 for sample addition, chromatographic development was allowed by leaving the device standing at room temperature for 30 minutes, and then for determining the presence or absence of capture of the complex of the ribosomal protein L7/L12 antigen and the gold colloid-labeled antibody by the aforementioned part 3 for capturing, a reddish purple line that became more or less conspicuous in proportion to the capture amount was measured by an apparatus C10066 (Hamamatsu Photonics). The ampholytic surfactant was added at different concentrations, and the lysis ratios for the concentrations were calculated as relative ratios to the lysis ratio of the cell suspension in which lysis treatment was performed beforehand in the same manner as that of Example 1, which was taken as 100%. The results are shown in FIG. 3. It was revealed that, with any of the ampholytic surfactants, the lysis ratio was markedly improved in a concentration-dependent manner.

Example 3

Measurement in Milk Sample by Immunochromatographic Method

An immunochromatographic method was performed for a milk sample obtained from a cow with mastitis. The measurement was performed in the same manner as that of Example 2 (lysis treatment solution contained 1% (final concentration) of Tween 20, 10 µg/ml (35 units/ml) of lysostaphin, 0.1 M MOPSO, pH 7.5, 0.1% (final concentration) of Zwettergent 3-12, the treatment was performed at room temperature for 30 minutes, and the development was performed at room temperature for 30 minutes), and the appeared reddish purple line was visually examined (positive +, negative −). Separately, in order to confirm the number of *Staphylococcus aureus* in the milk, quantification was performed by the cultivation-based method. Each milk sample (100 µl) was inoculated to Trypticase Soy Agar II with 5% Sheep Blood (Becton Dickinson Japan), then incubation was performed at 37° C. for 24 hours, and the colonies that appeared were counted. The numbers of *Staphylococcus aureus* calculated by the cultivation-based method, and determination results obtained by the immunochromatographic method are shown in Table 2. The addition of Zettergent 3-12 enabled detection of the bacteria of $10^3$ (cfu/ml) order.

TABLE 2

| Sample No. | Number of Staphylococcus aureus (cfu/ml) | Result of immunochromatography | |
|---|---|---|---|
| | | Without Zettergent 3-12 | With Zettergent 3-12 |
| 1 | $2 \times 10^2$ | − | + |
| 2 | $3 \times 10^2$ | − | + |
| 3 | $6 \times 10^2$ | − | + |
| 4 | $1 \times 10^3$ | − | + |
| 5 | $1 \times 10^3$ | − | + |
| 6 | $2 \times 10^3$ | − | + |
| 7 | $3 \times 10^3$ | + | + |

The invention claimed is:

1. A method for lysing a *staphylococcus* existing in milk, which comprises mixing a lysis agent comprising lysostaphin, an ampholytic surfactant, and a nonionic surfactant with the milk to lyse a *staphylococcus* existing in the milk, wherein a final concentration of the nonionic surfactant is not higher than 10% and a final concentration of the ampholytic surfactant is not higher than 0.5%.

2. The lysis method according to claim 1, wherein the ampholytic surfactant is selected from a dimethylammoniopropanesulfonate, a dodecyldimethylammoniobutyrate, lauryl betaine, and amidopropyl betaine; and/or the nonionic surfactant is selected from a polyoxyethylene alkyl phenyl ether and a polyoxyethylene sorbitan fatty acid ester.

3. The lysis method according to claim 1, wherein, in mixing the lysis agent with the milk to lyse a *staphylococcus* existing in the milk, wherein the final concentration of the ampholytic surfactant is not higher than 0.3%.

4. The lysis method according to claim 1, wherein, in mixing the lysis agent with the milk to lyse a *staphylococcus* existing in the milk, wherein the final concentration of the ampholytic surfactant is not lower than 0.03% and not higher than 0.5%.

5. The lysis method according to claim 1, wherein, in mixing the lysis agent with the milk to lyse a *staphylococcus* existing in the milk, wherein the final concentration of the ampholytic surfactant is not lower than 0.03% and not higher than 0.3%.

6. The lysis method according to claim 1, wherein, in mixing the lysis agent with the milk to lyse a *staphylococcus* existing in the milk, wherein a final concentration of lysostaphin is not lower than 0.1 μg/mL and not higher than 200 μg/mL; and/or in mixing the lysis agent with the milk to lyse a *staphylococcus* existing in the milk, the final concentration of the nonionic surfactant is not lower than 0.3% and not higher than 10%.

7. A method for detecting a *staphylococcus* contained in milk, which comprises
mixing a lysis agent comprising lysostaphin, an ampholytic surfactant, and a nonionic surfactant with the milk to lyse a *staphylococcus* existing in the milk, and
detecting a specific substance derived from inside of the *staphylococcus* and released by lysis,
wherein a final concentration of the nonionic surfactant is not higher than 10% and a final concentration of the ampholytic surfactant is not higher than 0.5%.

8. The detection method according to claim 7, which is performed by an immunochromatographic method.

9. The detection method according to claim 8, wherein the immunochromatographic method comprises:
(1) the step of contacting the milk containing the specific substance with a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a part existing upstream therefrom, and
(2) the step of flowing the milk up to the second part or a part existing downstream therefrom to obtain a detectable signal of the label at the second part or a part existing downstream therefrom.

10. The detection method according to claim 9, wherein the labeled first antibody directed to the specific substance is retained in the first part.

11. The detection method according to claim 9, wherein the third part is constituted by two or more kinds of members having voids that can remove milk fat globules of different particle sizes, respectively.

12. The detection method according to claim 11, wherein the third part is constituted by a first member disposed downstream and a second member disposed upstream, and retention particle size of the second member is larger than retention particle size of the first member.

13. The lysis method according to claim 1, wherein, in mixing the lysis agent with the milk to lyse a *staphylococcus* existing in the milk, wherein the final concentration of the ampholytic surfactant is not higher than 0.4%.

14. The lysis method according to claim 1, wherein, in mixing the lysis agent with the milk to lyse a *staphylococcus* existing in the milk, wherein the final concentration of the ampholytic surfactant is not lower than 0.3% and not higher than 0.4%.

15. The method for detecting a *staphylococcus* contained in milk, wherein the final concentration of the ampholytic surfactant is not higher than 0.4%.

16. The method for detecting a *staphylococcus* contained in milk, wherein the final concentration of the ampholytic surfactant is not lower than 0.03% and not higher than 0.4%.

* * * * *